US 6,734,140 B2

(12) United States Patent
Breau

(10) Patent No.: US 6,734,140 B2
(45) Date of Patent: May 11, 2004

(54) ALL-NATURAL MINERAL TREATMENT

(76) Inventor: Kenneth W. Breau, 8 Oxford Street, Brantford, Ontario (CA), N3R 5C6

( * ) Notice: Subject to any disclaimer, the term of this patent is extended or adjusted under 35 U.S.C. 154(b) by 67 days.

(21) Appl. No.: 10/051,444

(22) Filed: Jan. 18, 2002

(65) Prior Publication Data

US 2003/0104942 A1 Jun. 5, 2003

Related U.S. Application Data

(60) Provisional application No. 60/334,254, filed on Nov. 30, 2001.

(51) Int. Cl.$^7$ ............................ A01N 25/22; A01N 55/02
(52) U.S. Cl. ........................................ 504/150; 504/152
(58) Field of Search ................................. 504/150, 152

(56) References Cited

U.S. PATENT DOCUMENTS 6,149,821 A * 11/2000 Rounds et al. ............... 210/754
6,217,780 B1 * 4/2001 Denkewicz, Jr. et al. ... 210/764

* cited by examiner

*Primary Examiner*—S. Mark Clardy
(74) *Attorney, Agent, or Firm*—MacMillan, Sobanski & Todd, LLC

(57) ABSTRACT

The invention relates to a treatment for the control of algae in aquatic environments. The treatment includes an algicide in combination with at least one of a pH stabilizer, a clarifier, and a sanitizer reducer/enhancer.

20 Claims, No Drawings

ALL-NATURAL MINERAL TREATMENT

CROSS-REFERENCE TO RELATED APPLICATION

This application claims the benefit of U.S. Provisional Application Ser. No. 60/334,254, filed Nov. 30, 2001.

BACKGROUND OF THE INVENTION

This invention relates in general to the creation of an all-natural mineral treatment for the control of algae in pools, spas and hot tubs. This invention may also be used for other forms of water treatment such as pond, cooling towers or any such aquatic environment that algae is not desired. This invention is more than just an algicide; in different embodiments it also controls pH, clarifies water and/or reduces the demand for sanitization. Water chemistry can be a mystery, however we have attempted to reduce some of that mystery with this invention.

Water-soluble elemental copper, such as copper sulfate, is known to possess algicidal qualities when used in circulating water systems. Unfortunately, copper ions easily precipitate in alkaline or near-alkaline water conditions as insoluble salts of oxides, hydroxides, and/or carbonates, removing the copper from the system and thus removing the ability of the copper ion to act as an algicide.

In order to improve the efficacy of copper as an algicide, sequestering agents, such as alkanolamines, aminocarboxylic acids or citric acid have been used to improve the stability of copper in these conditions. These organic compounds contain amine, hydroxyl, and carboxyl functionalities that exhibit sequestration capacity for polyvalent cations.

Another problem encountered in water treatment applications, such as swimming pools, is that copper precipitates to form unsightly stains on the pool's surface. In particular, copper hydroxides, copper oxides and copper carbonates are known to cause unsightly stains that are difficult to remove.

A need therefore exists for a method of stabilizing soluble copper for longer periods of time during treatment and application, thereby increasing its effective life and preventing stains from occurring on swimming pool surfaces.

Another problem with existing copper products is the inability to control pH change, which will also cause copper to drop out of solution. Typically rain is very acidic in most parts of North America. When precipitation occurs, this acidic condition will cause the pH to "crash" below the tolerable limits required to maintain copper in solution, which will then cause the copper to create staining issues on pool and spa liners and accessories.

Typically copper's stability can also be affected by the interaction and contamination of foreign particles suspended in the water. If these particles are not eliminated, the sanitizer and algae control will be under greater demand.

The different embodiments of the present invention address all these needs.

SUMMARY OF THE INVENTION

The invention relates to a treatment for the control of algae in aquatic environments. The treatment includes an algicide such as copper-containing algicide. Preferably, the treatment also includes a mineral sequestering agent. In a typical use of the invention, the treatment can be used for the control of algae in the water of a swimming pool, spa or hot tub without staining the solid surfaces surrounding the water.

In one embodiment, the treatment includes an algicide and a pH stabilizer. Importantly, the treatment is able to control pH fluctuation that is typically caused by acidic rain. Acting very much like a shock absorber, the treatment will push the pH back to a neutral state automatically.

In another embodiment, the treatment includes an algicide and a clarifier. The treatment controls the amount of foreign material allowed to be suspended in the water. By using mineral based flocculants, the treatment is able to agglomerate these particles together, thereby allowing the filtration system to trap the particles. Reducing the number of foreign particles in the water will in turn reduce the demand loading on the sanitizer/algicide and provide the customer with clearer water.

In another embodiment, the treatment includes an algicide, a pH stabilizer, and a clarifier.

In another embodiment, the treatment includes an algicide and a sanitizer reducer/enhancer. This formulation contains properties that allow the sanitizer of choice to work in conjunction with this product. As the sanitizer works with this product they will be found to compliment each other therefore reducing the demand and consumption rates on the sanitizer of choice.

In another embodiment, the treatment includes an algicide, a clarifier, and a sanitizer reducer/enhancer.

In a further embodiment, the treatment includes an algicide, a pH stabilizer, and a sanitizer reducer/enhancer.

In a preferred embodiment, the treatment includes an algicide, a pH stabilizer, a clarifier, and a sanitizer reducer/enhancer. This embodiment will control algae, stabilize pH, clarify water, and compliment the sanitizer of choice.

DETAILED DESCRIPTION OF THE PREFERRED EMBODIMENTS

For the purposes of promoting an understanding of the principles of the invention, reference will now be made to preferred embodiments and specific language will be used to describe the same. It will nevertheless be understood that no limitation of the scope of the invention is thereby intended, such alterations and further modifications in the described device, and such further applications of the principles of the invention as illustrated therein being contemplated as would normally occur to one skilled in the art to which the invention relates.

As previously indicated, the invention relates to an improved treatment for the control of algae in aquatic environments. Any suitable algicide(s) can be used in the treatment composition. For purposes of this invention, the algicide is defined by the following U.S. Environmental Protection Agency definition: the EPA states that a pesticide (algicide) is any substance or mixture of substances intended for use as a plant regulator, defoliant, or desiccant and therefore will control algae in lakes, canals, swimming pools, water tanks, and other sites. The definition includes all pesticide products under the Federal Insecticide, Fungicide, and Rodenticide Act (FIFRA), including those used for antimicrobial purposes. Preferably, the algicide is elemental copper, which can be provided as copper sulfate or as soluble or insoluble copper salts such as copper acetate, copper chloride, copper formate and copper carbonate.

Preferably, the treatment includes a mineral sequestering agent to stabilize the copper even in alkaline environments and prevent its loss due to precipitation, thereby increasing the effective life of the algicide and preventing staining of swimming pool surfaces. Soluble elemental copper is easily removed from solution through filtration and by combining with carbonate and hydroxide ions that are commonly found in process water, such as swimming pools, to form insoluble copper carbonates and hydroxides. Sequestered copper does not readily form these insoluble salts or filter out of the system. Thus, sequestered copper has a higher residence time in the pool. This allows the copper to work for longer periods of time. In certain preferred embodiments organic acids such as, e.g., oxalic acid, succinic acid, and maleic acid, and the salts thereof, are used as the sequestering agent. Especially preferred are the hydroxy-carboxylic acids such as, e.g., citric acid, gluconic acid, tartronic acid, tartaric acid, malic acid, or tetrahydroxy succinic acid, and the salts thereof, and the lactone forms of such acids. The organic acids and hydroxy-acids are preferred in certain embodiments because the other noted sequestering agents are sources of nitrogen and phosphorous, two critical nutrients for algae growth.

In one embodiment, the treatment also includes a pH stabilizer along with the algicide. The pH stabilizer is able to control pH fluctuation that is typically caused by acidic rain. Acting very much like a shock absorber, the treatment will push the pH back to a neutral state automatically. For purposes of this invention, the pH stabilizer is defined as one or more materials that reduces the effects from outside sources changing the pH level of the particular aquatic environment we are attempting to stabilize. Typically pH will be affected by acidic rain, introduction of water from a source outside of the controlled environment or airborne particles. PH adjustment and control can be done with sodium carbonate, sodium bicarbonate, and calcium carbonate or other pH adjusters. The uniqueness of this our stabilization is the fact that we have created a shock absorber that will actually push the pH back to an acceptable range, preferably to a pH within the range of about 6.8 to about 7.6, more preferably about 7.2 to about 7.4.

In another embodiment, the treatment includes a clarifier in combination with the algicide. The clarifier improves water clarity by binding very small particles together which in turn when enough are bound together they create a larger piece of matter that is able to be trapped by the filtration system. The clarifier reduces the amount of free particulate suspended in the water. Any suitable clarifier or combinations thereof can be used. For example, mineral flocculants can be used as the clarifier, such as aluminum sulfate and/or aluminum potassium sulfate.

In a further embodiment, the treatment includes a sanitizer reducer/enhancer in combination with the algicide. The sanitizer reducer/enhancer has properties that will increase the performance and effectiveness of the sanitization method being used. Typically it is very difficult to retain a balanced level of sanitizer in water. This problem is magnified with the effects of ultraviolet rays from the sun. These rays can actually breakdown the sanitizer and deplete it from the water very quickly. Traditional sanitizers that are used can be chlorine, bromine, ionization, ozone generators, saltwater chlorinators and other methods for bacteria control. The sanitizer reducer/enhancer binds the free sanitizer, creating a stabilized environment for the sanitizer to be interconnected with the treatment composition. This can be accomplished with any suitable material or combination of materials, for example, anionic surfactants, sodium carbonate, sodium bicarbonate, calcium carbonate, sodium chloride, aluminum sulphate, aluminum potassium sulphate and citric acid.

A surfactant can also be used in the treatment composition to break the surface tension of the water, which makes the composition dissolve better and avoids clumping of the product on the surface.

Most preferably, the treatment composition includes a combination of an algicide, a pH stabilizer, a clarifier, and a sanitizer reducer/enhancer. In a particular embodiment, the treatment composition includes the following ingredients: water-soluble anionic surfactants, copper sulphate, sodium carbonate, sodium bicarbonate, calcium carbonate, sodium chloride, aluminum sulphate, aluminum potassium sulphate and citric acid.

Some preferred ranges of these ingredients are as follows:
Copper Sulfate from 5.85% to 20.10%.
Sodium Chloride from 8.40% to 18.35%.
Anionic surfactant from 0.20% to 1.50%.
Citric Acid from 0.00% to 24.04%.
Aluminum Potassium Sulfate from 0.00% to 6.75%.
Aluminum Sulfate from 0.00% to 5.80%.
Calcium Carbonate from 6.20% to 14.50%.
Sodium Bicarbonate from 0.00% to 40.70%.
Sodium Carbonate from 0.00% to 10.80%.

Some typical ranges of these ingredients are as follows:
Copper Sulfate from 9.50% to 16.90%.
Sodium Chloride from 10.40% to 16.35%.
Anionic surfactant from 0.50% to 1.11%.
Citric Acid from 16.15% to 20.04%.
Aluminum Potassium Sulfate from 2.40% to 5.15%.
Aluminum Sulfate from 1.91% to 4.50%.
Calcium Carbonate from 7.35% to 12.17%.
Sodium Bicarbonate from 26.43% to 37.10%.
Sodium Carbonate from 5.50% to 7.88%.

EXAMPLE 1

Preparation of Composition:

Copper Sulfate 20.10%. Sodium Chloride 12.50%. Anionic surfactant 0.71%. Citric Acid 18.40%. Aluminum Potassium Sulfate 4.20%. Aluminum Sulfate 1.20%. Calcium Carbonate 6.20%. Sodium Bicarbonate 31.70%. Sodium Carbonate 4.99%. This formulation yields a blue/white powder that contains 4.98% elemental copper.

EXAMPLE 2

Preparation of Composition:

Copper Sulfate 11.13%. Sodium Chloride 14.37%. Anionic surfactant 0.50%. Citric Acid 15.74%. Aluminum Potassium Sulfate 1.90%. Aluminum Sulfate 1.89%. Calcium Carbonate 14.27%. Sodium Bicarbonate 34.98%. Sodium Carbonate 5.22%. This formulation yields a blue/white powder that contains 2.75% elemental copper.

EXAMPLE 3

Preparation of Composition:

Copper Sulfate 9.13%. Sodium Chloride 10.37%. Anionic surfactant 0.80%. Citric Acid 13.00%. Aluminum Potassium Sulfate 6.75%. Aluminum Sulfate 4.34%. Calcium Carbonate 6.31%. Sodium Bicarbonate 40.70%. Sodium Carbonate 8.60%. This formulation yields a blue/white powder that contains 2.26% elemental copper.

EXAMPLE 4

Preparation of Composition:

Copper Sulfate 7.13%. Sodium Chloride 13.52%. Anionic surfactant 0.20%. Citric Acid 17.40%. Aluminum Potassium Sulfate 3.90%. Aluminum Sulfate 5.80%. Calcium Carbonate 8.20%. Sodium Bicarbonate 37.80%. Sodium Carbonate 6.05%. This formulation yields a blue/white powder that contains 1.76% elemental copper.

EXAMPLE 5
Preparation of Composition:

Copper Sulfate 5.85%. Sodium Chloride 8.40%. Anionic surfactant 1.00%. Citric Acid 22.50%. Aluminum Potassium Sulfate 3.90%. Aluminum Sulfate 1.80%. Calcium Carbonate 6.25%. Sodium Bicarbonate 39.50%. Sodium Carbonate 10.80%. This formulation yields a blue/white powder that contains 1.45% elemental copper.

EXAMPLE 6
Preparation of Composition:

Copper Sulfate 15.00%. Sodium Chloride 18.35%. Anionic surfactant 1.50%. Citric Acid 20.92%. Aluminum Potassium Sulfate 2.80%. Aluminum Sulfate 2.80%. Calcium Carbonate 9.00%. Sodium Bicarbonate 21.65%. Sodium Carbonate 7.98%. This formulation yields a blue/white powder that contains 3.71% elemental copper

EXAMPLE 7
Preparation of Composition:

Copper Sulfate 18.40%. Sodium Chloride 8.40%. Anionic surfactant 1.10%. Citric Acid 24.04%. Aluminum Potassium Sulfate 3.26%. Aluminum Sulfate 3.40%. Calcium Carbonate 9.00%. Sodium Bicarbonate 28.20%. Sodium Carbonate 4.20%. This formulation yields a blue/white powder that contains 4.55% elemental copper.

EXAMPLE 8
Preparation of Composition:

Copper Sulfate 13.13%. Sodium Chloride 14.37%. Anionic surfactant 0.8%. Citric 25 Acid 17.4%. Aluminum Potassium Sulfate 3.9%. Aluminum Sulfate 2.8%. Calcium Carbonate 9.0%. Sodium Bicarbonate 31.7%. Sodium Carbonate 6.9%. This formulation yields a blue/white powder that contains 3.25% elemental copper.

EXAMPLE 9
Preparation of Composition:

Copper Sulfate 16.45%. Sodium Chloride 12.74%. Anionic surfactant 0.98%. Citric Acid 21.50%. Aluminum Potassium Sulfate 3.90%. Aluminum Sulfate 2.40%. Calcium Carbonate 14.50%. Sodium Bicarbonate 20.63%. Sodium Carbonate 6.90%. This formulation yields a blue/white powder that contains 4.07% elemental copper.

EXAMPLE 10
Preparation of Composition:

Copper Sulfate 19.70%. Sodium Chloride 15.79%. Anionic surfactant 0.98%. Citric Acid 21.50%. Aluminum Potassium Sulfate 0.00%. Aluminum Sulfate 0.00%. Calcium Carbonate 14.50%. Sodium Bicarbonate 20.63%. Sodium Carbonate 6.90%. This formulation yields a blue/white powder that contains 4.88% elemental copper.

EXAMPLE 11
Preparation of Composition:

Copper Sulfate 19.80%. Sodium Chloride 17.58%. Anionic surfactant 0.98%. Citric Acid 0.00%. Aluminum Potassium Sulfate 3.90%. Aluminum Sulfate 3.35%. Calcium Carbonate 14.50%. Sodium Bicarbonate 39.89%. Sodium Carbonate 0.00%. This formulation yields a blue/white powder that contains 4.90% elemental copper.

EXAMPLE 12
Preparation of Composition:

Copper Sulfate 19.98%. Sodium Chloride 18.22%. Anionic surfactant 1.49%. Citric Acid 23.75%. Aluminum Potassium Sulfate 6.65%. Aluminum Sulfate 5.79%. Calcium Carbonate 13.34%. Sodium Bicarbonate 0.00%. Sodium Carbonate 10.78%. This formulation yields a blue/white powder that contains 4.95% elemental copper.

The treatment composition of the invention is typically manufactured in granular and tabletized formats.

The treatment composition is very effective in the control of algae. The efficacy of the invention has been documented with laboratory studies under Good Laboratory Practices to the United States Environmental Protection Agency and the California Department of Pesticide Regulation. Further tests were done using test swimming pools and spas infested with algae. This water was treated with this invention to a concentration of 0.7 to 0.5 ppm. All the water treated with the formulation of the invention killed the algae.

The development of this invention has taken a significant amount of time and effort, because we needed to perform a large number of test batches to determine the correct blend. There can be a number of potential problems when developing an invention this unique. First we needed to determine an acceptable level of copper required to not only eliminate algae but also control it. It is very important to understand there are a number of different types of algae. The most common types of algae are green yellow, brown, red and black as well other unique strains. Once the level of copper was determined we needed to properly kelate the copper to keep it from coming out of solution and creating staining issues on pool liners and accessories. Typically algicides are manufactured and sold in a liquid format, which makes kelation much easier to perform in a controlled manufacturing environment. This invention is unique because our product is in a dry solid/granular state. Therefore our need to utilize the water in which we are treating as part of the chemical reaction for kelation.

Being an algicide is not the only uniqueness in our invention. pH stability is also a very important factor when considering chemical stability in aquatic environments. A very unique property with this invention is our shock absorber that is built into our chemistry that will actually push the pH level back up to a pH neutral range (typically 7.2). This is done under the theory that every action should generate an equal and opposite reaction. For example when the pH is push down by acid rain our invention will automatically work harder and counter-react this force by pushing the pH back to a pH neutral range. This is very unique as pH adjustment is typically done manually by adding soda ash or muratic acid to adjust the pH up or down. What we have created with this invention is a product that uses mineral technology to control this automatically. We have only been able to develop this after many test batches to perfect the chemistry to a point that we were comfortable in making the claim on our container and satisfying the United States Environmental Protection Agency and the California Department of Pesticide Regulation.

The clarification process was somewhat easier to control and develop. As we had given ourselves a mandate when we stated to design this invention we wanted to create an All-Natural Mineral Treatment. Therefore we needed to determine a type of flocculent that could serve this purpose at the same time meeting our mandate. After trial and errors with a number of different type of flocculants/clarifiers, we settled on using aluminum base products.

The sanitizer enhancement portion of our product is again unlike any other product in the marketplace. Many specialty chemicals (especially algicides) make claims they are able to reduce the consumption of sanitizer. This is simply due to the fact that when any product such as an algicide is used, it will reduces the demand load on a sanitizer. Our invention not only does this but our invention also binds the molecular structure of the water together to reduce the amount of sanitizer that is evaporated from the water. This inventions chemically altering phenomenon occurs when it is applied to the water. There is a visible chemical reaction that occurs at this point in time. From that point in time the water structure has changed to repel the effects from ultraviolet rays hence a better sanitizer and a much smaller dosage rate required to maintain the bacteria kill rates.

As stated earlier water chemistry is and can be very mysterious. What we expect to happen does not always occur. This being said, we would like to be very clear this type of formulation does not occur by simply blending randomly selected quantities of ingredients. The amount of different combinations in quantities can be staggering when you look at the number of ingredients we have selected. Having said this, it took literally thousands of different batches to refine this invention to the level that it is effective, stable and constant with different water qualities across North America. During our testing years we had sent samples of this invention to many different locations across North America for evaluation. Typically we would encounter different problems in each area. After we reviewed the data we went back to the drawing board and adjusted the formula and again sent out a different batch for testing. This occurred many times until we were satisfied that we had finally achieved our initial objectives that were stated in the claims portion of this document.

While the invention has been illustrated and described in detail in the foregoing description, the same is to be considered as illustrative and not restrictive in character, it being understood that only the preferred embodiment has been shown and described and that all changes and modifications that come within the spirit of the invention are desired to be protected.

What is claimed is:

1. A treatment for the control of algae in aquatic environments comprising an algicide in an amount of from 5.85% to 20.10% by weight of the treatment, and a pH stabilizer.

2. A treatment according to claim 1 further comprising a surfactant.

3. A treatment according to claim 1 wherein the treatment does not include a sanitizer.

4. A treatment for the control of algae in aquatic environments comprising an algicide in an amount of from 5.85% to 20.10% by weight of the treatment, a clarifier, and a surfactant.

5. A treatment according to claim 4 wherein the clarifier is present in an amount of less than 12.55% by weight of the treatment.

6. A treatment according to claim 4 wherein the treatment does not include a sanitizer.

7. A treatment for the control of algae in aquatic environments comprising an algicide in an amount of from 5.85% to 20.10% by weight of the treatment, a pH stabilizer, and a clarifier.

8. A treatment according to claim 7 wherein the clarifier is present in an amount of less than 12.55% by weight of the treatment.

9. A treatment according to claim 7 further comprising a surfactant.

10. A treatment according to claim 7 wherein the treatment does not include a sanitizer.

11. A treatment for the control of algae in aquatic environments comprising an algicide in an amount of from 5.85% to 20.10% by weight of the treatment, and a sanitizer reducer/enhancer.

12. A treatment according to claim 11 further comprising a surfactant.

13. A treatment according to claim 11 wherein the treatment does not include a sanitizer.

14. A treatment for the control of algae in aquatic environments comprising an algicide in an amount of from 5.85% to 20.10% by weight of the treatment, a clarifier, and a sanitizer reducer/enhancer.

15. A treatment according to claim 14 wherein the clarifier is present in an amount of less than 12.55% by weight of the treatment.

16. A treatment according to claim 14 wherein the treatment does not include a sanitizer.

17. A treatment for the control of algae in aquatic environments comprising an algicide in an amount of from 5.85% to 20.10% by weight of the treatment, a pH stabilizer, and a sanitizer reducer/enhancer.

18. A treatment according to claim 17 wherein the treatment does not include a sanitizer.

19. A treatment for the control of algae in aquatic environments comprising an algicide in an amount of from 5.85% to 20.10% by weight of the treatment, a pH stabilizer, a clarifier, and a sanitizer reducer/enhancer.

20. A treatment according to claim 19 wherein the clarifier is present in an amount of less than 12.55% by weight of the treatment, and wherein the treatment does not include a sanitizer.

* * * * *